(12) United States Patent
Pas et al.

(10) Patent No.: US 8,525,386 B2
(45) Date of Patent: Sep. 3, 2013

(54) DYNAMICALLY ADJUSTABLE ORTHOTIC DEVICE

(75) Inventors: Sylvia D. Pas, Richardson, TX (US); Michael F. Pas, Richardson, TX (US)

(73) Assignee: Texas Instruments Incorporated, Dallas, TX (US)

( * ) Notice: Subject to any disclaimer, the term of this patent is extended or adjusted under 35 U.S.C. 154(b) by 869 days.

(21) Appl. No.: 12/634,263

(22) Filed: Dec. 9, 2009

(65) Prior Publication Data

US 2011/0131838 A1 Jun. 9, 2011

(51) Int. Cl.
*H01L 41/09* (2006.01)
*H01L 41/107* (2006.01)
*H01L 41/113* (2006.01)
*H01L 41/18* (2006.01)

(52) U.S. Cl.
USPC ............ 310/314; 310/317; 310/319; 310/338

(58) Field of Classification Search
USPC ........................... 310/314, 317–319, 338, 339
See application file for complete search history.

(56) References Cited

U.S. PATENT DOCUMENTS

| | | | |
|---|---|---|---|
| 4,814,661 A * | 3/1989 | Ratzlaff et al. | 310/328 |
| 5,033,291 A | 7/1991 | Podoloff et al. | |
| 5,631,861 A * | 5/1997 | Kramer | 703/7 |
| 5,813,142 A * | 9/1998 | Demon | 36/29 |
| 6,201,889 B1 | 3/2001 | Vannah | |
| 6,718,656 B2 | 4/2004 | Houser et al. | |
| 6,809,462 B2 * | 10/2004 | Pelrine et al. | 310/319 |
| 6,882,086 B2 | 4/2005 | Kornbluh et al. | |
| 6,969,365 B2 | 11/2005 | Scorvo | |
| 7,056,297 B2 * | 6/2006 | Dohno et al. | 601/48 |
| 7,219,449 B1 | 5/2007 | Hoffberg et al. | |
| 7,321,185 B2 | 1/2008 | Schultz | |
| 7,391,123 B2 | 6/2008 | Rome | |
| 7,426,873 B1 * | 9/2008 | Kholwadwala et al. | 73/818 |
| 7,458,173 B2 | 12/2008 | Kielt et al. | |
| 7,548,010 B2 | 6/2009 | Browne et al. | |
| 7,997,007 B2 * | 8/2011 | Sanabria-Hernandez | 36/1 |
| 8,141,277 B2 * | 3/2012 | Robinson et al. | 36/137 |
| 2003/0145495 A1 | 8/2003 | Green | |
| 2007/0180737 A1 | 8/2007 | DiBenedetto et al. | |

* cited by examiner

*Primary Examiner* — Thomas Dougherty
(74) *Attorney, Agent, or Firm* — Alan A. R. Cooper; W. James Brady; Frederick J. Telecky, Jr.

(57) ABSTRACT

An orthotic device comprises a flexible support structure comprising at least one surface for contacting a body part of a user, a plurality of pressure sensors configured for coupling to a microcontroller, and a plurality of displacement regions. Each region defines a portion of said flexible support structure, wherein each portion includes at least one sensor disposed on or below the at least one surface and at least one electrically deformable unit. Each unit comprises at least one electroactive material and is configured for coupling to the microcontroller and to a power source. The device is dynamically adjustable to change its shape and support properties, when an electrical voltage is applied to the electroactive material under the control of a microcontroller.

22 Claims, 6 Drawing Sheets

DYNAMICALLY ADJUSTABLE ORTHOTIC DEVICE

FIELD OF THE INVENTION

This invention generally relates to orthotic devices and, more particularly, to such devices containing shape memory materials and piezoelectric sensors for dynamically adjusting the support characteristics of the device with the aid of a microprocessor.

BACKGROUND

Specialized orthotic devices, sometimes referred to as "orthodics," are currently in use in a wide variety of applications relating to musculoskeletal support, reinforcement, correction, enhancement and toning. Such devices are often in the form of a shoe insert for relieving or correcting some type of foot problem, as might arise, for example, from congenital abnormality, injury, disease or surgery. Typically, foot orthodics are customized to an individual's foot through an iterative trial-and-error process, which usually requires multiple sets of orthodics to be produced and which may not have the desired result. Most solutions for foot orthotic problems rely on devices made of a hardened composite material that is formed from a mold of the individual's foot. These devices are then modified by heating an adhesive and physically adding to, or removing material from, the device by trial and error to provide proper support. Iterative processes are often expensive and, in many cases, the device that is finally obtained is not satisfactory nor solve the underling problem. Customized orthotic devices designed to support or reinforce other external parts of the body, such as knee, wrist, shoulder, elbow and ankle, to an individual user's specific needs have similar challenges. Accordingly, there is continuing interest in developing orthotic devices that are more easily and accurately fitted to the individual user and which provide the desired functional support or reinforcement and are dynamically adjustable.

SUMMARY

In accordance with certain embodiments of the invention, an orthotic device is provided that comprises: a flexible support structure comprising at least one surface for contacting a body part of a user; a plurality of pressure sensors configured for coupling to a microcontroller; and a plurality of displacement regions. Each region constitutes or defines a portion of the flexible support structure, and each portion includes at least one of the sensors disposed on or below the at least one surface, and also includes at least one electrically deformable unit (e.g., a unimorphic or multi-morphic structure). Each unit comprises at least one electroactive material and is configured for coupling to the microcontroller and to a power source. In some embodiments, one or more pressure sensor comprises a piezoelectric material capable of emitting an electrical voltage when depressed.

In certain embodiments, each displacement region has a respective first physical configuration when an electrical voltage is not applied to the deformable unit, and has a second physical configuration when an electrical voltage is applied to the deformable unit. For example, the second physical configuration increases physical support for a portion of the body part contacting the device compared to the first physical configuration.

Also provided in accordance with certain embodiments is an orthotic module comprising an above-described orthotic device, a microcontroller electrically coupled to the orthotic device, and a power source electrically coupled to the orthotic device and to the microcontroller. In some embodiments the module also includes an analog to digital converter coupled between the orthotic device and the microcontroller, and includes a digital to analog converter coupled between the microcontroller and the orthotic device.

A method of adjusting a dynamically adjustable orthotic device is also provided in accordance with certain embodiments. The method comprises a) coupling an above-described device to a microcontroller and a power source; b) causing an individual in need of an orthotic device to be positioned so that an external body part of the individual contacts the at least one surface of the device; c) causing the body part to move and exert pressure on the at least one surface sufficient to depress at least one the sensor, causing each depressed sensor to emit a respective electrical signal indicative of the pressure; d) operating the microcontroller to measure each the electrical signal, wherein each such measurement is correlated to a physical address of a respective sensor and deformable unit in a said region and includes electrical properties and elapsed time between measurements; e) operating the microcontroller to determine from the measurements whether any region requires structural modification to increase or decrease physical support for a portion of the body part in contact with the device; and f) based on the determination, applying an electrical voltage to at least one deformable unit in a region determined to require the increased physical support, and/or decreasing or ceasing application of an electrical voltage to at least one deformable unit in a region determined to require the decreased physical support, to change the configuration of the orthotic device. In some embodiments, the method includes f) repeating steps b)-e) to adjust the orthotic device during further movement of the body part by the individual, to provide a dynamically adjusted orthodic. In some embodiments of an above-described method the body part is a foot of the individual and b)-e) are performed during movement of the foot. In some embodiments, after executing step e), an electrical voltage is continuously applied to lock the orthotic device into an adjusted configuration.

In accordance with still another embodiment of the invention, an orthodic is provided which is manufactured by a process comprising obtaining a locked orthodic in accordance with an above-described method, producing a mold from the locked orthotic device; and applying a resilient polymeric material to the mold to form a permanent orthotic device.

According to another embodiment, a dynamically adjustable orthotic module is provided which comprises a flexible support structure comprising at least one surface for contacting a body part of a user; a plurality of pressure sensors; and a plurality of displacement regions, each such region defining a portion of the flexible support structure. Each such portion includes at least one said sensor disposed on or below the at least one surface, and at least one electrically deformable unit. Each such unit comprises at least one electroactive material. The module further comprises a microcontroller electrically coupled to the flexible support structure; and a power source electrically coupled to the flexible support structure and microcontroller. In some embodiments, the module further comprises an analog to digital converter coupled between the flexible support structure and the microcontroller; and a digital to analog converter coupled between the microcontroller and the flexible support structure.

In accordance with still another embodiment of the invention, a method of dynamically adjusting an orthotic module is provided which comprises a) causing an individual in need of an orthotic device to be positioned so that an external body part of the individual contacts the at least one surface of an above-described module; b) causing the body part to move and exert pressure on the at least one surface sufficient to depress at least one said sensor, causing each depressed sensor to emit a respective electrical signal indicative of the pressure; c) operating the microcontroller to measure each said electrical signal, wherein each such measurement is correlated to a physical address of a respective sensor and deformable unit in a said region and includes electrical properties and elapsed time between measurements; d) operating the microcontroller to determine from the measurements whether any region requires structural modification to increase or decrease physical support for a portion of the body part in contact with the at least one surface; e) based on the determination, applying an electrical voltage to at least one deformable unit in a region determined to require such increased physical support, and/or decreasing or ceasing application of an electrical voltage to at least one deformable unit in a region determined to require such decreased physical support, to change the configuration of the orthotic device; and f) repeating steps b)-e) during further movement of the body part by the individual. In some embodiments the orthotic module is configured for supporting a foot of the user. In some embodiments, the power source comprises an air bladder-wind turbine power generator mounted in the shoe of the user.

Also provided in accordance with certain embodiments of the invention is a foot powered energy harvesting device comprising: a shoe including a chamber, at least a portion of which is surrounded by an electrically conductive coil; a resilient air bladder disposed in the chamber and containing at least one air inlet valve and at least one air outlet; at least one air turbine disposed in the chamber, each of which is connected to a respective air outlet, the air turbine and having blades disposed on a rotatable shaft with magnets thereon, wherein the coil and air turbine are configured to generate electricity when air is expelled from the air bladder outlet causing the shaft to rotate. In certain embodiments, the energy harvesting device further includes an energy storage device coupled to the coil. These and other embodiments, features and potential advantages will be apparent in the drawings and the following description.

BRIEF DESCRIPTION OF THE DRAWINGS

For a detailed description of exemplary embodiments of the invention, reference will now be made to the accompanying drawings, which are not necessarily drawn to scale, in which:

FIG. 2A is a top down view of an innersole-type orthodic like that of FIG. 1, showing separate displacement regions or zones associated with respective sensors in the flexible support structure, according to an embodiment of the invention. FIG. 2B is a side view of an orthodic with a 3-dimensional, boot-like flexible support structure containing sensors and hinged displacement regions.

FIG. 3A illustrates hinged regions. FIG. 3B is a cross-sectional side view of an orthodic containing the hinged regions of FIG. 3A, with two regions independently deformed.

FIG. 4A shows a unimorph structure. FIG. 4B shows a bimorph structure.

DEFINITIONS

Certain terms are used throughout the following description and claims to refer to particular system components. As one skilled in the art will appreciate, companies may refer to a component by different names. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct electrical connection. Thus, if a first device couples to a second device, that connection may be through a direct electrical connection, or through an indirect electrical connection via other devices and connections.

The term "orthotics" refers to the technical field of design, development, fitting and manufacture of devices ("orthoses") that are used to support or align the human body, especially when the body is in motion.

The terms "orthosis," "orthotic device" and simply "orthotic" or "orthodic" are used interchangeably herein, and refer to a device or appliance used to support the human body, especially when the body is in motion, and in some instances is designed to correct or ameliorate a musculoskeletal abnormality.

An "electroactive material" is a material that mechanically deforms, changes shape or displaces when a sufficient voltage is applied. More specifically, an electroactive material may change shape, stiffness, position, natural frequency, physical displacement and/or other mechanical property in response to application of an electric field. An example of an electroactive material is polyvinylidene fluoride (PVDF). In some instances, an electroactive material is a "piezoelectric material" which produces a small electrical voltage when it is mechanically deformed (e.g., is forced to change shape under applied mechanical pressure).

A "unimorph" or "unimorphic structure" refers to a single layer of electroactive material and associated electrodes.

A "multi-morph" or "multi-morphic structure" refers to two or more stacked layers of electroactive material and associated electrodes. The materials forming each layer may be the same or different. A multi-morph having two stacked layers is termed a "bimorph."

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Figure 1:
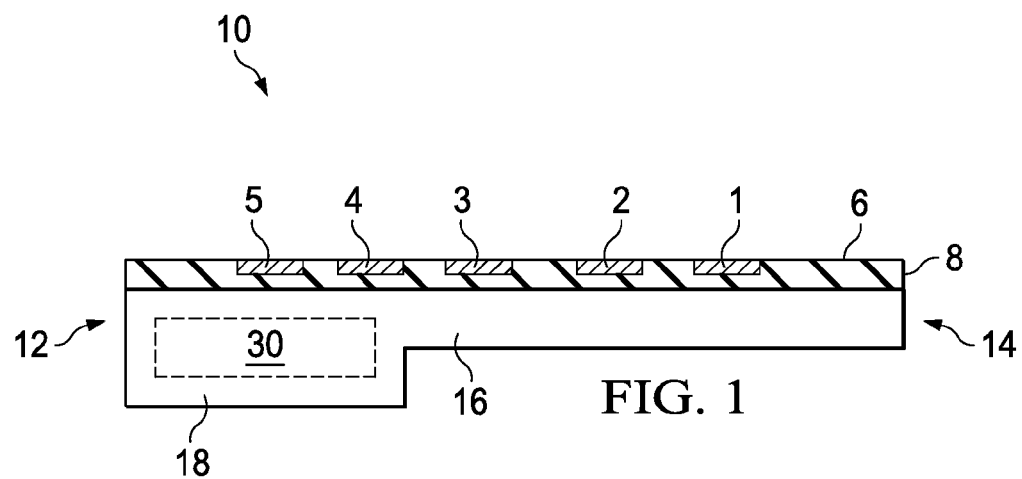
FIG. 1 is a side cross-sectional view of an orthodic according to an embodiment of the invention.
Figure 2A:
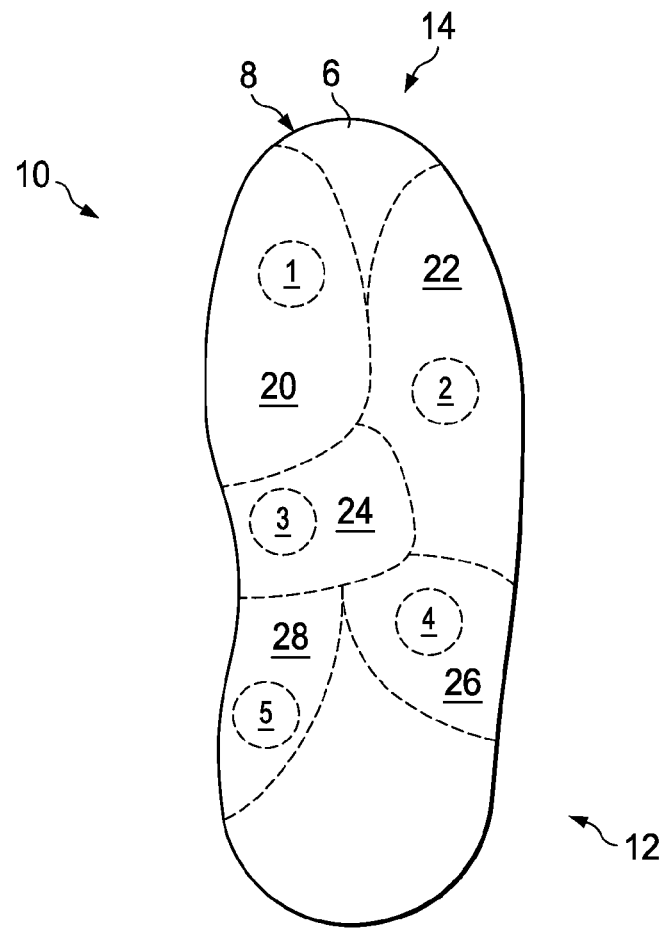
FIGS. 2A-B illustrate embodiments of a flexible support structure for an orthotic.
Figure 2B:
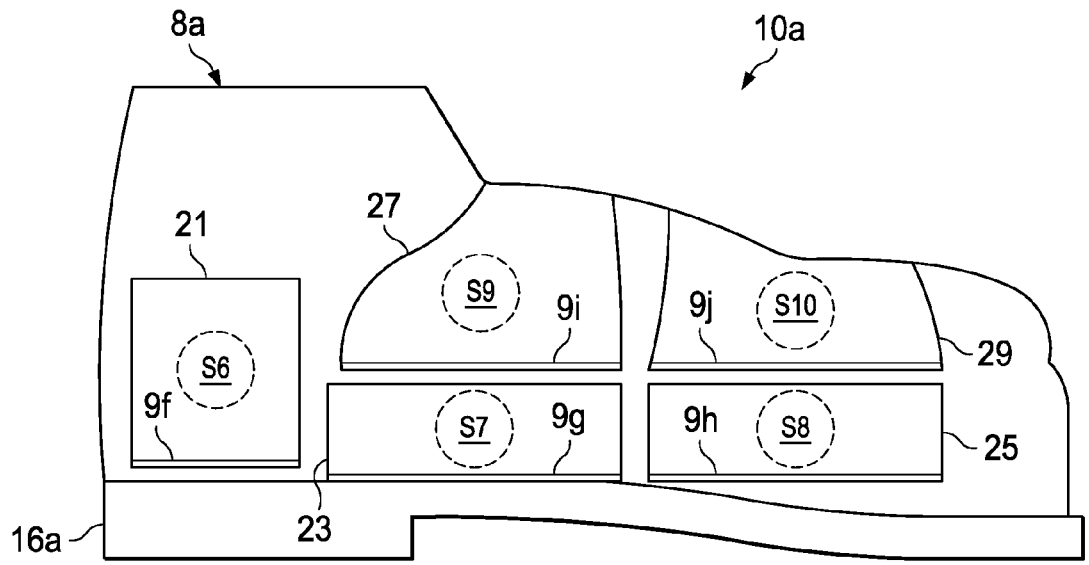
Figure 3A:
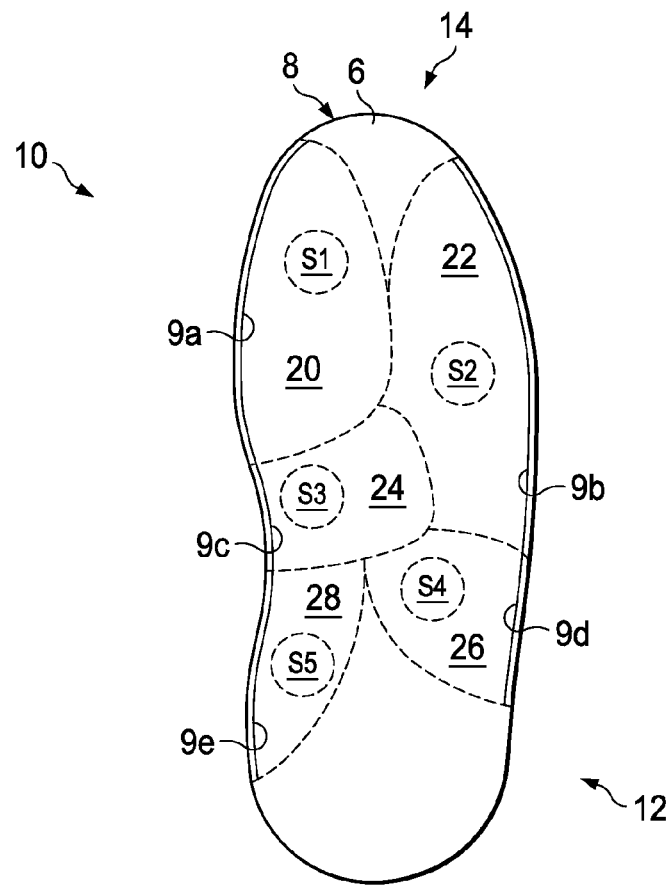
FIGS. 3A-B illustrate an orthodic like that of FIG. 1, with each region anchored at one edge to provide for independent deformation and movement of each region.

FIGS. 1, 2A and 3A illustrate embodiments in which an orthodic 10 comprises a plurality of sensors 1-5 disposed on surface 6 of flexible support structure (FSS) 8 (sometimes referred to as layer 8). Alternatively, the sensors are embedded in the FSS (e.g., just below surface 6). Orthodic 10 includes a toe end 14 and a heel end 12. In some embodiments orthodic 10 also includes a sole 16 which has a heel portion 18 (FIG. 2). As discussed in more detail below, in some applications, the orthodic is combined with a controller package 30 which may be located in the heel of the wearer's shoe or may be part of a self-contained orthodic unit, as illustrated in FIG. 1. In some cases an orthodic is configured as a shoe innersole or insert such as an arch support suitable for placing inside a shoe over an existing sole and heel of the wearer's shoe. FIG. 2 illustrates a top down view of an orthodic 10 showing surface 6 and an array of associated sensors 1-5 positioned at intervals from toe end 14 to heel end 12. The flexible support structure is divided into multiple electrically-isolated segments, each of which serves as a separately deformable region or zone. An embodiment of an orthodic 10 in which the FSS 8 is divided into separate regions or zones 20-28, each of which is associated with a respective sensor 1-5. Each region has a segment of flexible support structure configured for electrically coupling to a digital to analog (D/A) converter that is configured to couple to a microcontroller. Each region 20-28 may have a unique size and shape, as shown in FIG. 2A. Alternatively, the regions may in some cases be of uniform size and shape. Each region contains a unimorphic- or multi-morphic structure containing at least one electroactive material and associated electrodes and circuitry for coupling to a microcontroller and power source. Neighboring regions are electrically isolated from each other by a flexible insulating material, as described in more detail below.

Similar to FIG. 2A, an embodiment of a boot-like orthotic device 10a is shown in FIG. 2B, in which each region 21, 23, 25, 27 and 29 is attached at one side to an outer boundary or side edge of the FSS 8a, so that each region is free to move independently (e.g., like a hinged flap), relative to neighboring regions or portions of the FSS via respective hinges 9f-9j. Not visible in FIG. 2B is a corresponding set of regions and sensors on the opposite side of device 10a. Also not visible in FIG. 2B is an innersole-like portion of the FSS similar to that shown in FIG. 2A.

FIG. 3A shows an FSS like that of FIG. 1, with regions 20, 22, 24, 26 and 28 hinged by respective hinges 9a-9e, in which regions 22 and 28 are selectively deformed and are upwardly displaced independently of the neighboring FSS regions.

Figure 4A:
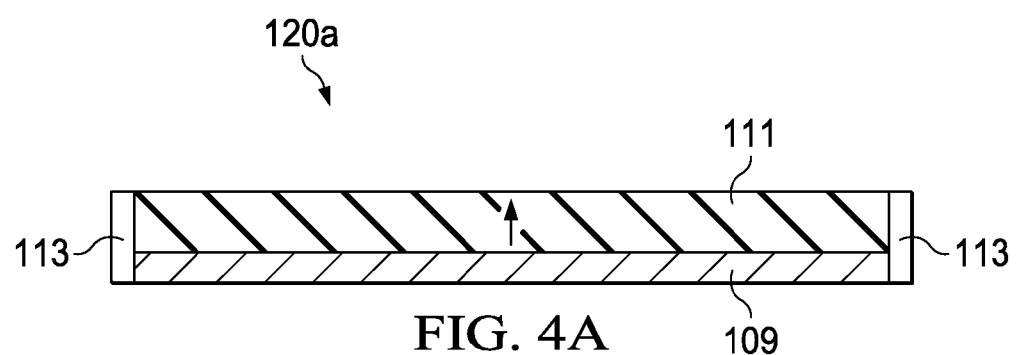
FIGS. 4A-B are schematic illustrations of deformable units used in the displacement regions of the orthodic of FIG. 3, according to certain embodiments of the invention.
Figure 4B:
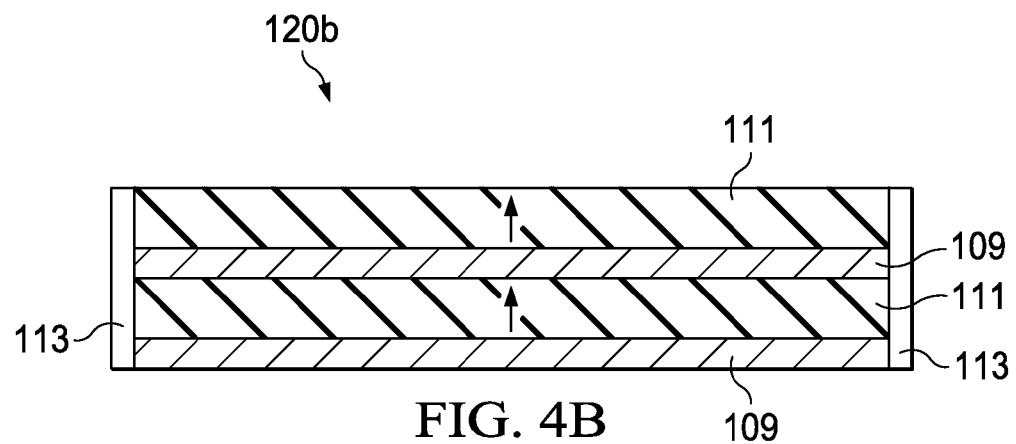

Each of the above-described displacement regions contains at least one deformable unit. A unimorphic deformable unit is schematically illustrated in FIG. 4A, and a multi-layer or multi-morphic deformable unit is represented by the bimorph shown in FIG. 4B. As shown in FIGS. 4A-B, each deformable unit 120a, 120b includes insulating caps 113 at the ends of each unimorph and multi-morph. Unimorphs and multi-morphs are described in more detail below. In some cases the thickness and other dimensions of orthodic 10 are similar to those of a conventional arch support or innersole. The number and thickness of the layers in orthodic 10 and its overall dimensions are determined based on the maximum expected pressure and depression distance that the device is desired to measure and the amount of displacement of the flexible support structure that is desired in a particular application. For example, a device for a child will generally not be as thick as a device designed for use by an adult or a corrective device may be more rigid than a supportive device. The orthodic may have any shape or physical conformation that is suitable for the desired placement during use. For example, as illustrated in FIG. 2A, in some cases the FSS may be shaped like a shoe innersole for preparing a foot orthodic such as an arch support. Orthodic 10 is also dynamically adjustable, i.e., the shape and/or support characteristics of the device are capable of being adjusted to an improved configuration while the device is being worn by the individual.

In some embodiments, the FSS is configured as a three-dimensional, boot-like structure with sensors arranged over all or a portion of the interior surfaces that will contact the top, bottom, heel and sides of the individual's foot, for three-dimensional sensing of pressure points on the foot when the individual is at rest or during motion, as shown in FIG. 2B. In combination with an appropriately programmed microcontroller and a power source, the FSS is capable of dynamically adjusting regions that contact the bottom, heel, sides and top of the individual's foot.

FIG. 2B shows a side view of a boot-like orthodic 10a with an FSS 8a attached to a sole 16, similar to FIG. 1. The FSS may include an innersole-type portion similar to that shown in FIG. 1. FSS 8a includes sensor S6 arranged for sensing pressure from the heel of an individual's foot, sensors S7 and S8 for sensing pressure from areas on a side of the foot, and sensors S9 and S10 for sensing pressure from portions of the top of the foot. Corresponding regions 21-29 are constructed and arranged to provide increased or decreased support to portions of the foot, when an electrical voltage is applied or modified. Similar to the embodiment of FIG. 3A, each region is attached or anchored to the FSS structure (e.g., by respective hinges 9f-9j) so that each region can shape-shift independently as directed by the microcontroller.

In addition to foot orthodics, in some embodiments orthotic devices for use in other types of applications are designed in accordance with the same principles as described herein with respect to a foot orthodic. Such other devices include, but are not limited to, orthopedic neck braces, pillows, and bedding to relieve pressure points on the individual's body. Similarly, in some embodiments, a mattress is configured to include an orthotic device capable of being re-adjusted to change pressure points over time to alleviate medical issues (e.g., avoid bed sores).

Figure 3B:
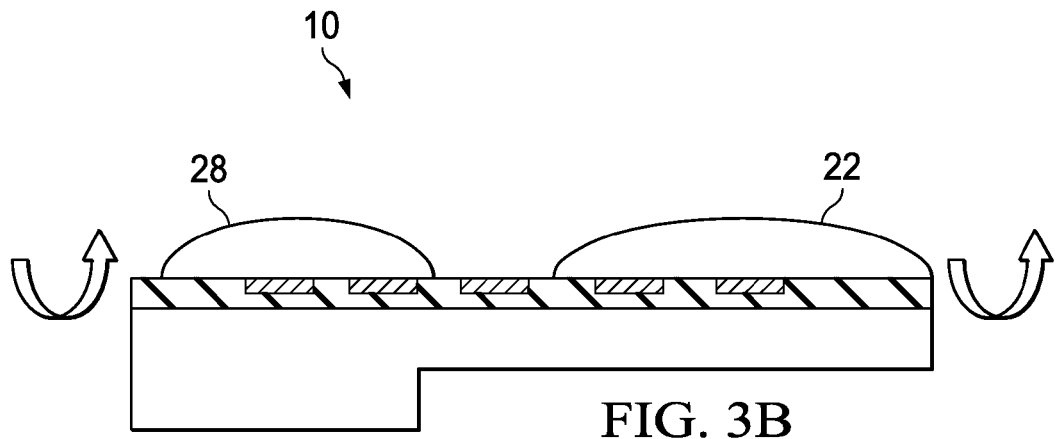
Figure 5:
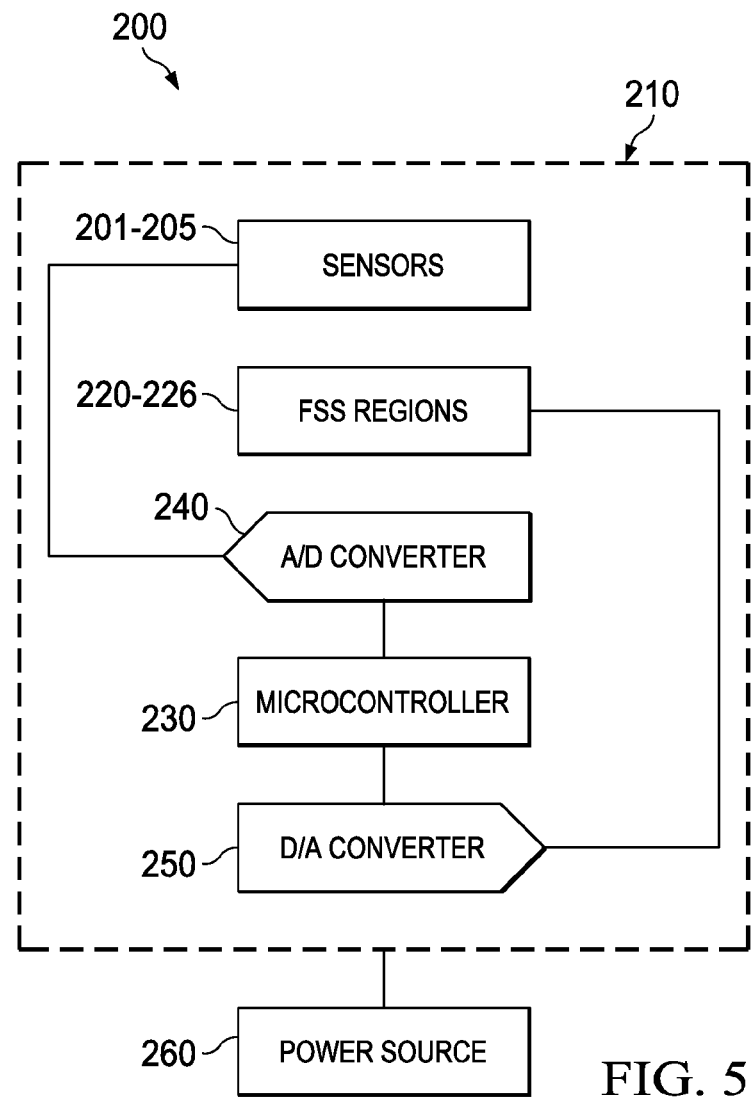
FIG. 5 is a schematic block diagram of a dynamically adjustable orthodic system according to an embodiment of the invention.

In FIG. 5, a system 200 is illustrated as a schematic box diagram. System 200 contains an orthodic 210, which in some embodiments is like that shown in FIGS. 1-3, which includes two or more sensors 201 and FSS regions 220. Also included in system 200 are microcontroller 230, power source 260, ND converter 240 and D/A converter 250 and any associated circuitry. Sensors 201 of orthodic 210 are coupled to an analog to digital (ND) converter 240 and FSS regions 220 of orthodic 210 are coupled to a digital to analog (D/A) converter 220. Microprocessor or microcontroller 230 is coupled between ND converter 240 and D/A converter 250. A power source 260 is coupled to one or more components of system 200. In some applications, at least the FSS regions and sensors of orthodic 210 are combined to form a self-contained modular system or unit. For example, the power source 250, ND and D/A converters 240, 250 and microcontroller 230 may be located in the heel of the wearer's shoe (as illustrated by controller package 30 in FIG. 1). In other applications the power source 250 and/or the microcontroller 230 are not contained in the same structure as the other components of orthodic 210. For example, in some cases the power source may be mounted elsewhere on a shoe. In some cases the microcontroller 230 is connected to a conventional power grid as the power source 260 rather than to a battery or other portable power source. Any suitable ultra low power microprocessor may be used as microcontroller 230. In some embodiments, a Texas Instruments MSP430 ultra low power microprocessor is used. Due to the low power requirements for operating the device and microprocessor, in some embodiments an entire module may be powered by a battery (e.g., a Li ion battery) or a capacitor, or self-powered by the motion of the foot.

Figure 7:
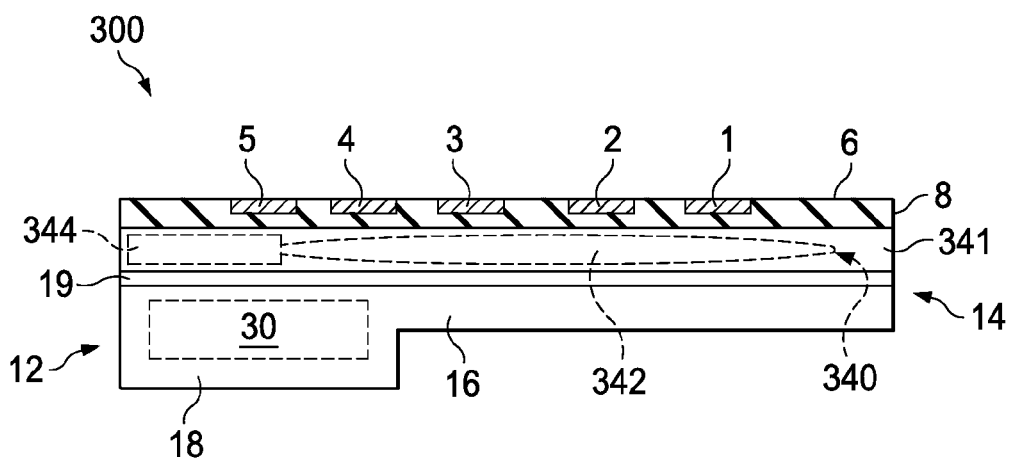
FIG. 7 is a side cross-section view of a dynamically adjustable orthodic module with an air bladder-wind turbine power generator, according to an embodiment of the invention.

In some embodiments, a shoe mounted energy harvesting mechanism is utilized as the power source in an orthotic system. An exemplary shoe-mounted air bladder/air turbine energy harvesting system is illustrated in FIG. 7 and described in more detail below. Alternatively, any other suitable shoe-mounted energy harvesting technology described in the literature may be adapted for this purpose, if desired. For example, a piezoelectric or induction energy harvesting assembly embedded into the heel or the bottom of an orthotic insert or shoe may be used to supply energy directly to the orthotic module, or to charge a battery or capacitor. In some applications, the motion of walking will either depress or reset the piezoelectric element or push up or down a spring loaded magnet induction based energy harvesting method.

Pressure Sensors. In some embodiments of an orthotic device the pressure sensors contain a piezoelectric (PE) material. The PE sensor is designed to emit a small voltage when sufficient pressure is applied to it, such as occurs when a person steps down on the orthodic. Each burst of voltage corresponds to the amount of physical deformation that occurs. Piezoelectric materials have the physical property of discharging voltage indicating that it detected a pressure when its physical shape deforms due to a pressure. The piezoelectric material of the sensors may be a crystalline material, a ceramic material, or a piezoelectric polymer. Some suitable piezoelectric materials for use as pressure sensors include but are not limited to the following: quartz crystal, poly crystal ceramic, and gallium phosphate, and polyvinylidenefluoride (PVDF). The sensors are electrically isolated from the flexible support structure of layer 8. This may be accomplished, for example, by coating each sensor with a flexible insulative material. In some embodiments, one or more sensor comprises a resistor or pressure sensor instead of a piezoelectric material to detect pressure applied to various regions of an orthodic.

As illustrated in FIG. 1, in some embodiments the sensors are imbedded in the electroactive material of the flexible support structure 8, and may be positioned adjacent the surface 6. Alternatively, in some embodiments the sensors are contained in a separate layer adhered to the surface 6 of layer 8.

Unimorphic- and Multi-morphic Structures. Electroactive materials are used as displacement materials in the FSS of an orthotic device disclosed herein. Flexible support structure (FSS) 8 of the embodiment shown in FIG. 1 comprises one or more electroactive materials that change shape, stiffness, position, natural frequency, physical displacement and/or other mechanical property in response to application of an electrical voltage. The yield strength of an FSS and its physical deformation or displacement properties are exploited in the design of the present orthotic devices. A deformable unit (FIG. 4A-B) of a FSS displacement region (as shown in FIGS. 2A-B and 3A-B) is constructed so as to deliver a force under electrical excitation greater than that exhibited under no electrical excitation.

The shape or support property of selected regions of an orthodic is altered by virtue of an electrical voltage-induced strain of an active material in a selected deformable unit within a region of the orthodic. The shape and/or modulus properties, such as flexural properties and shear strength, of the active material is selectively varied by application of suitable voltage.

Referring to FIGS. 4A-B, in some embodiments, a deformable unit 120*a* of a displacement region (e.g., region 20 in FIG. 2) of a flexible support structure (like that shown in FIG. 1B) comprises a single layer of electroactive material 111 and an associated electrode 109, and is referred to as a unimorphic structure, or unimorph (FIG. 4A). In another embodiment, a displacement region 120*b* comprises one or more multi-morphic structures, each comprising a "sandwich" of two or more layers of electroactive material 111, together with associated electrodes 109. A two-layer multi-morph structure is referred to as a bimorphic structure or bimorph, as illustrated in FIG. 4B. The electroactive material in the unimorph or multi-morph deforms or displaces according to the input of the pressure sensors, the calculations of the microcontroller, and the resulting electric voltage that is applied to a particular displacement region of the flexible support structure.

FIG. 4B illustrates schematically a bimorph 108 comprising two polymer films 111 deposited between film electrodes 109. In some multi-morph structures, an insulating film such as epoxy is disposed between each unimorph unit in a series of stacked unimorphs. In some applications, the thin electrodes are metal (Ni alloy such as Ni 81% Fe permalloy). In some applications, a bimorph contains two piezoelectric polymer films (e.g., polyvinylidenefluoride or PVDF) deposited between the thin metal electrodes. In FIGS. 4A-B, the large arrows indicate the direction of displacement or deformation of the PE films when an electrical voltage is applied to the films, in certain applications. In some embodiments, the direction of displacement is opposite to the direction shown in FIGS. 4A-B when the polarity of the electrodes is reversed. While the extent of deformation or displacement of a single layer of electroactive material is typically in the range of tens of microns, when multiple layers of deformable units are sandwiched together and a voltage is applied, a multi-morphic structure may, in some cases, deform up to several centimeters depending on the number of layers and the level of applied voltage.

Electroactive Material.

Suitable electroactive materials for the above-described deformable units include, but are not limited to, shape memory alloys, magneto restrictive materials, ferroelectric materials, shape memory polymer, piezoelectric materials and electroactive polymers. In some cases, an electroactive polymer is a piezoelectric polymer. In some cases a piezoelectric material comprises a piezoceramic (e.g., lead zirconate titanate) or a piezocomposite. Some suitable electroactive polymers include, but are not limited to, poly(sodium 4-styrenesulfonate), poly(poly(vinylamine) backbone azo chromophore), and their derivatives; polyfluorocarbons (e.g., polyvinylidenefluoride, its co-polymer vinylidene fluoride ("VDF"), co-trifluoroethylene, and their derivatives); polychlorocarbons (e.g., poly(vinyl chloride), polyvinylidene chloride, and their derivatives); polyacrylonitriles and their derivatives; polycarboxylic acids (e.g., poly(methacrylic acid), and their derivatives); polyureas and their derivatives; polyurethanes and their derivatives; polyanilines and their derivatives, and all of the derivatives of tetramines; polyamides including aromatic polyamides and polyimides (e.g., Kapton and polyetherimide, and their derivatives); membrane-forming polymers (e.g., poly(N-vinyl pyrrolidone) (PVP) homopolymer, and its derivatives, and random PVP-co-vinyl acetate copolymers; aromatic polymers with dipole moment groups in the main-chain or side-chains, or in both the main-chain and the side-chains, and mixtures thereof. In certain embodiments, the electroactive polymer is polyvinylidene fluoride (PVDF).

In some embodiments the electroactive material comprises one or more of the following metals: lead, antimony, manganese, tantalum, zirconium, niobium, lanthanum, platinum, palladium, nickel, tungsten, aluminum, strontium, titanium, barium, calcium, chromium, silver, iron, silicon, copper. In some embodiments, the electroactive material comprises an alloy of one or more of the aforesaid alloys. In some embodiments, the electroactive material comprises at least one metal oxide of an aforesaid metal. In various embodiments, the electroactive material comprises $SiO_2$, $Al_2O_3$, $ZrO_2$, $TiO_2$, $SrTiO_3$, $PbTiO_3$, $BaTiO_3$, $FeO_3$, $Fe_3O_4$, ZnO, or a mixture of any of those oxides. In some embodiments, the electroactive material comprises at least one compound containing one or more Group VIA and IIB element of the Periodic Table of the Elements (e.g., CdSe, CdS, GaAs, $AgCaSe_2$, ZnSe, GaP, InP and ZnS, and mixtures thereof). In some embodiments the piezoelectric material comprises lead zirconate titanate, and barium titanate, or a mixture of those.

Suitable electroactive shape memory alloy materials include, but are not limited to, nickel-titanium based alloys, indium-titanium based alloys, nickel-aluminum based alloys, nickel-gallium based alloys, copper based alloys (e.g., copper-zinc alloys, copper-aluminum alloys, copper-gold, and copper-tin alloys), gold-cadmium based alloys, silver-cadmium based alloys, indium-cadmium based alloys, manganese-copper based alloys, iron-platinum based alloys, iron-palladium based alloys, and the like. The alloys can be binary, ternary, or any higher order so long as the alloy composition exhibits a shape memory effect, e.g., change in shape orientation, changes in yield strength, and/or flexural modulus properties, damping capacity, superelasticity, and the like, in response to application of an electrical voltage to the material. In some embodiments, the shape memory alloy is a nickel-titanium based alloy (e.g., FLEXINOL, a product of Dynalloy, Inc.).

In some embodiments, electroactive polymers include those polymeric materials that exhibit piezoelectric properties in response to an applied electrical voltage. Materials suitable for use as an electroactive polymer may include any substantially insulating polymer or rubber (or combination thereof) that deforms in response to applied electrical voltage. Non-limiting examples of such materials include silicone elastomers, acrylic elastomers, polyurethanes, thermoplastic elastomers, copolymers comprising PVDF, pressure-sensitive adhesives, fluoroelastomers, polymers comprising silicone and acrylic moieties, and co-polymers and combinations of those.

The selected electroactive material is activated by means of an applied activation voltage, which results in a change in the material's modulus or shape properties. In some embodiments, combinations of electroactive materials are used.

Modular Orthotic Unit. In some embodiments, the dynamically adjustable orthotic device is in the form of a self-contained or modular unit that will be directly used by the individual as the "permanent" orthotic, as illustrated in FIG. 1, for example. In this case, the electroactive material is adjusted or re-structured as needed over time, without being removed from the individual's shoe, for example. When electrical power is continuously supplied to the device, the desired support configuration is maintained and the orthotic is capable of dynamically re-adjusting to the individual's foot during use, to maintain the optimal shape, support and resiliency characteristics. A battery or other shoe mounted power source may be used to provide the necessary electric power for this embodiment.

Diagnostic Orthotic Device. In some embodiments, an above-described dynamically adjustable orthotic device is designed for primarily diagnostic use rather than therapeutic use. In this case, once the optimal configuration of the diagnostic device has been determined for an individual's foot, the flexible support structures are locked into place by providing an appropriate constant electrical voltage to the desired regions, and the optimally configured device is then used as a model for forming the final orthotic from other, lower cost, materials to cushion and hold the correct shape of the final product (i.e., the orthotic to be worn by the individual). Thus, the pressure points on the individual's foot are sensed electronically and the input used to modify the memory material electronically, and the modification or manufacturing of a custom-fitted orthotic is done based on data rather than based on a conventional time consuming, iterative touch-and-feel process. This embodiment has potential advantages for use in a medical office or an orthotics store as a diagnostic tool that is not necessarily configured for placement in the individual's shoe and may be plugged into a standard electrical outlet rather than requiring a portable power source. The diagnostic device may have any suitable dimensions, and is necessarily limited as to size or shape by the need to fit into the individual's shoe.

In some applications, the initial configuration of the orthotic is generated digitally in an actual use situation without manual intervention between the digital data and actual orthotic device. In some embodiments, the input is obtained and 3-dimensional data generated using any suitable technique for obtaining a three-dimensional topographic map of an object. For example, the method described in U.S. Pat. No. 6,201,880 may be used in some embodiments to obtain a digitized 3-D topographic map of a foot of an individual in need of an orthotic device.

Shoe-mounted Energy Harvesting Device. The ability to power portable electronic devices has conventionally relied on batteries. The use of batteries is usually satisfactory over a short period of time (e.g., less than one month) in an environment where recharging is possible. In some embodiments, a conventional battery such as a Li ion battery is used to power an above-described orthotic device. However, for long term (i.e., months) of use a renewable source of power is desirable in many cases. For example, for powering a dynamically adjustable orthotic device 210 or a modular system 200 (FIG. 5), repetitive foot motion (i.e., walking or running) is converted into electricity to be used as power source 260 in some instances. Referring to FIG. 7, device 340 comprises a resilient air bladder 342 containing at least one air inlet valve and at least one air outlet valve (not shown), and at least one air turbine 344 connected to a respective air outlet of the bladder. The air turbine 344 comprises blades disposed on a rotatable shaft which has magnets on it (not shown). Device 340 is designed to generate electricity, in cooperation with a surrounding electrically conductive coil, when air is expelled from the air bladder outlet through the turbine, causing the shaft to rotate. The air inlet and outlet valves may be standard bypass valves as are known in the art.

One way to take advantage of repetitive foot motion to power a modular orthodic 300 includes placing an air bladder/wind turbine device 340 into a shoe-mounted orthodic similar to that shown in FIG. 1. The air bladder/wind turbine device 340 is disposed in chamber 341 between the sole 16 and an inside lining 19 of the shoe. At least a portion of chamber 341 is surrounded by an electrically conductive coil (not shown), which in some embodiments are embedded in the walls defining chamber 341, together with associated electrical circuitry. The air bladder 342 and the wind turbine are disposed inside chamber 341, with the coil surrounding at least the wind turbine portion of device 340, operably positioned for producing electricity when air is expelled from the air bladder outlet into the wind turbine, causing the shaft to rotate the magnets within the coil.

The bladder is formed of a flexible, resilient material that allows it expand and to be filled with air during the up motion of the foot, and to be compressed during the downward motion of the foot, causing the air to be forced out of the bladder via a conventional one-way valve (not shown).

When the shoe-mounted orthodic 300 is in use, air is drawn into the bladder through a one-way valve (not shown). The air bladder is made of rubber, latex, plastic, or any other material that is suitable for this purpose. The air exiting the bladder is forced through a small turbine 344 in which a central drive shaft is connected to a permanent magnet (not shown). Electricity is generated by induction due to the spinning turbine. Adjacent circuitry (not shown) transports the produced electricity to the desired device (e.g., orthodic 210). The bladder is sufficiently flexible and resilient that when the foot is not in contact with the ground the bladder automatically fills with air through the air inlet valve, but is prevented from escaping through the inlet during expulsion of the air from the bladder. In some embodiments, expansion of the air bladder and filling it with air is aided by a spring located inside the bladder. Likewise, the bladder outlet valve is configured to remain closed during air intake by the bladder. A small turbine MEMS airflow harvester such as that described in Vol. 96, No. 9, September 2008 Proceedings of the IEEE, pg. 1457, for example, is suitable for use over an air flow speed range of about 0.5-100 m/s, providing a power density (mW/cm$^2$) of about $10^{-4}$-$10^4$, which is sufficient in many embodiments for generating the energy needed to operate the dynamically adjustable orthodic. The electricity produced by device 340 is either used immediately or is stored for use later in a small rechargeable Li ion battery or a capacitor 30 which is coupled to the coil and located in the heel 12 of shoe-mounted orthodic 300.

In a variation of the design shown in FIG. 7, the air bladder/wind turbine device comprises two turbines positioned at opposite ends of the air bladder, each turbine connected to a one-way air outlet of the bladder. One or more one-way air inlet is located at any suitable site or sites on the air bladder. In some embodiments, the coil surrounds at least the turbines, and the turbines are configured to turn in opposite directions so that the electricity produced by each can be readily combined and conducted to the orthotic device or to the storage means.

Figure 6:
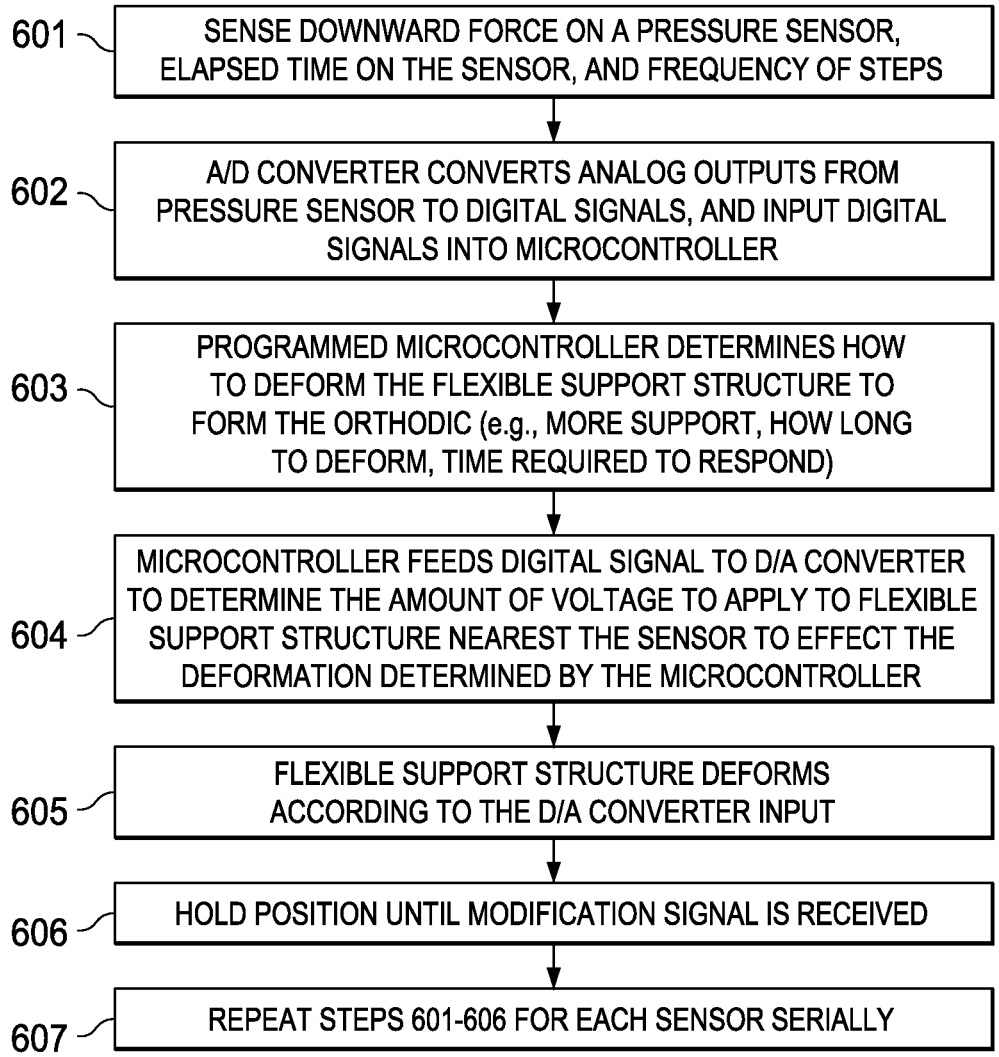
FIG. 6 is a block flow diagram illustrating a method of dynamically adjusting an orthodic according to an embodiment of the invention.

Method of Dynamically Adjusting an Orthotic Device. Referring to FIG. 6, in some embodiments an above-described diagnostic orthotic device designed for measuring the pressure points of an individual's foot during rest and/or in motion, is used to dynamically adjust the orthotic to the individual's foot. Sets of pressure measurements are obtained when the person stands, walks and/or runs, as the foot contacts and depresses sensors corresponding to various regions of the orthodic. The individual stands and bears weight on the foot, which presses down on the surface of the diagnostic device (FIGS. 1 and 2A). When a three-dimensional or boot-like FSS (FIG. 2B) is used, the sides and top of the individual's foot contact other interior surfaces having additional sensors. In so doing, the various sensors of the orthodic are depressed to varying degrees in correspondence with different pressure points on the individual's foot. In some embodiments, the sensor comprises a piezoelectric material which generates a voltage (analog signal) indicating it has been pressed and the extent to which its physical shape has been deformed. Additional measurements may be taken and recorded during various stages of motion of the foot, e.g., during walking and running. The diagnostic process generally includes the following steps, indicated by boxes 601-607 in FIG. 6:

(601) Sensing the downward force on a pressure sensor, sensing the elapsed time on the sensor, and the frequency of steps (i.e., the pace or time interval between steps while walking, etc.).

Figure 8:
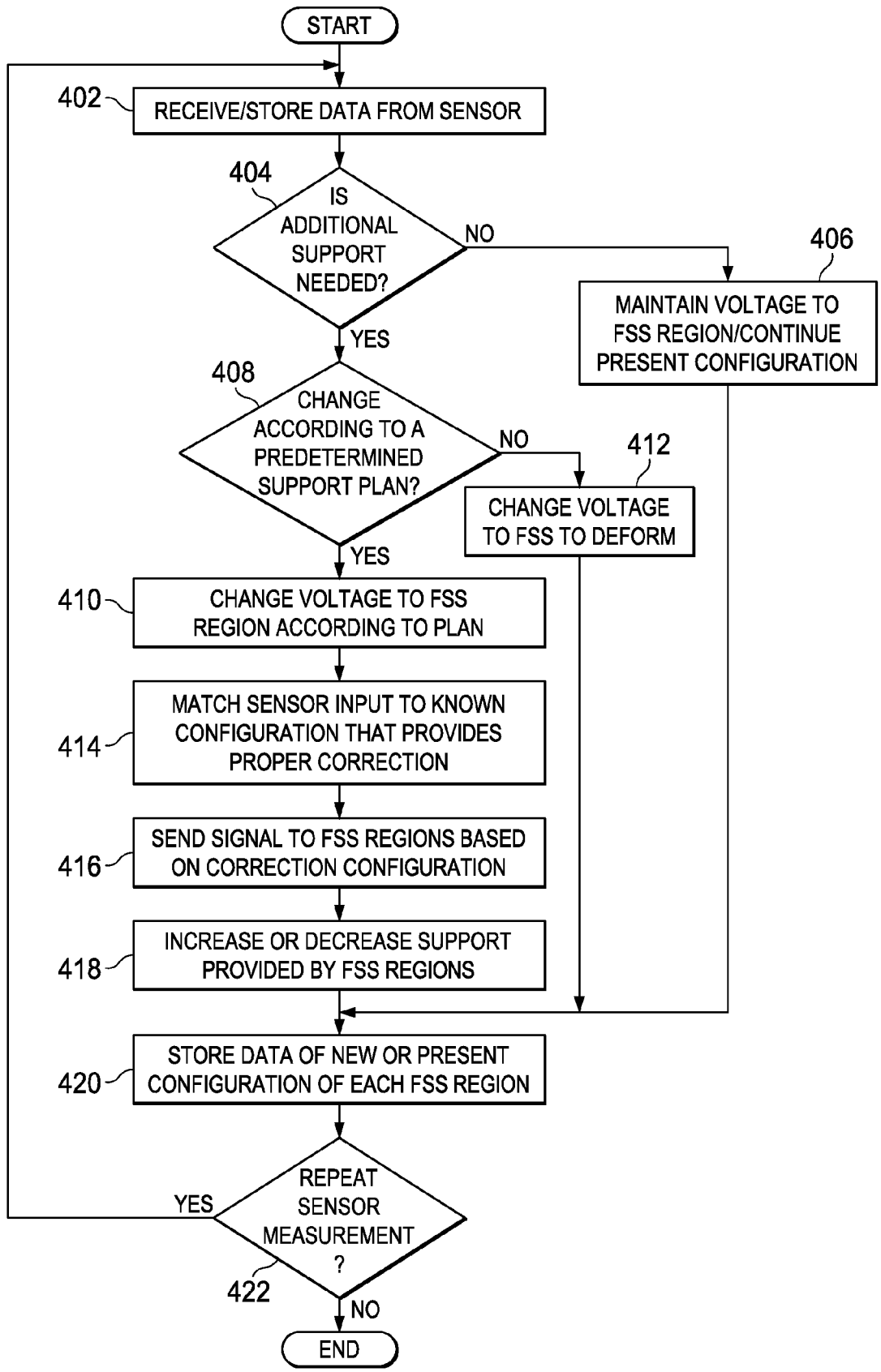
FIG. 8 schematically illustrates a microcontroller algorithm for adjusting an orthotic device according to an embodiment of the invention.

(602) The emitted signal is conducted to an ND converter, where the output from the sensor is converted to digital signals. The resulting digital signals are input into a microcontroller, where the sensor's signal characteristics, including physical address of the sensor, are identified and stored in the microcontroller. The physical address of each sensor correlates with a particular FSS region, as illustrated in FIG. 4. The sensed data measurements are recorded by the microcontroller, which is programmed with a suitably tuned algorithm, as illustrated in FIG. 8, for example.

(603) The programmed microcontroller determines how to deform the flexible support structure to form the orthodic. In some embodiments, the microcontroller determines where more support is needed, how long to deform the FSS of a particular region of the orthodic to achieve the necessary support, and if any delayed response time is appropriate. For example, after every step, every other step, every third step, the microcontroller is to adjust the orthodic (e.g., to provide additional support in certain regions, if needed).

(604) The microcontroller determines the amount of voltage to apply and feeds the calculated digital signal to digital/analog (D/A) converter to one or more deformable units in a displacement region corresponding to (e.g., nearest) the sensor, to effect the deformation determined by the microcontroller. Thus, using the pressure measurements processed according to the algorithm, the microcontroller causes respective electrical voltages to be applied to the electroactive material of the selected region or regions.

(605) The selected region of the flexible support structure deform according to the DA converter input, causing the shape of the orthotic to change as determined by the microcontroller.

(606) The adjusted position of the selected displacement region is maintained until a modified voltage is applied to that region.

(607) The preceding steps are repeated for each of the sensors, in serial fashion, for example.

The microcontroller is programmed to analyze the measurements to determine whether the individual's foot needs more or less support, or if the positioning of any portion of the foot should be changed to affect body alignment, and, if so, exactly where it is needed. For example, in some cases more support may be needed at the arch or ball of the foot. Automatically, or in response to an initiating signal, the microcontroller causes the D/A converter to apply a respective voltage to one or more deformable units (FIGS. 4A-B) of the FSS regions (FIG. 2A-B or 3A-B), causing each electroactive layer or film to either expand (e.g., by a millimeter or so), or compress itself, in response to the applied voltage, or to the reduction or cessation of an applied voltage. Thus, pressure points on the individual's foot are sensed electronically and the input to the microprocessor is used to electronically modify the mechanical properties of one or more deformable unit in one or more region of FSS 8. The modifications are made based on data rather than using a more expensive and/or time consuming conventional iterative touch-and-feel process. In this manner, the new orthotic device is dynamically adjusted to a second, or improved, configuration while the device is being worn by the individual.

An exemplary microcontroller algorithm is shown in FIG. 8, in which, for each sensor input (402), the microcontroller stores data (e.g., pressure, pace); decides whether additional pressure should be applied or released (404). If no additional support is needed, the microcontroller sends a signal (406) to maintain the existing configuration (i.e., maintains the voltage to the deformable units of a selected FSS region). If it is determined that additional support is needed in a selected FSS region, the microcontroller sends a signal to one or more deformable units in a selected FSS displacement region (i.e., changes the voltage to the selected units) to increase support in the selected region. In some embodiments, the microcontroller determines whether additional pressure should be applied based on a predetermined support plan (408). If no predetermined support plan is used, the desired voltage is applied to the FSS regions (412) based on the sensor input. If a predetermined support plan is selected (410), this may include matching input from one or more sensors to a known configuration that will provide proper correction (414). The microcontroller then sends a signal to the selected deformable units based on the correction configuration (416). The microcontroller then adjusts the voltage of the selected deformable units to increase or decrease support of selected FSS displacement regions (418) based upon sensor input. The microcontroller stores data (420) regarding the new configuration of each deformable unit of each FSS region after step 412 or 418. In instances in which the outcome of query 404 is that no additional support, or no change in support is needed, the present configuration data is also stored (420). This sequence is repeated (422) for each sensor measurement. In some embodiments, the algorithm and method may be varied to permit simultaneous sensing of two or more sensors, and simultaneous processing of the sensed data.

In some embodiments, a predetermined support plan is derived from a digitized three-dimensional topographic image of the individual's foot, which is correlated to preset voltage settings for specific displacement regions and for specific deformable units. A configuration that will provide proper correction for that individual's foot is derived from this digital 3-D image, and serves as the "known configuration" referred to in the foregoing algorithm. Alternatively, in some embodiments, a predetermined support plan is obtained by executing the above-described algorithm and increasing or decreasing the voltage applied to a selected deformable unit in defined increments, to increase or decrease displacement, until repeated sensing indicates that the desired displacement configuration has been achieved and that no further changes are necessary.

Referring to the 3-D, boot-like embodiment illustrated in FIG. 2B, an embodiment of a method of adjusting an orthotic device according to a predetermined support plan includes first, taking a three-dimensional image of the foot using any suitable technique for obtaining a three-dimensional topographic map of an object. Next, the resulting three-dimensional image of the foot is fed to the orthotic device's microcontroller, and then one or more displacement regions of FSS 8a are adjusted so as to match the 3-D image of the foot.

The above discussion is meant to be illustrative of the principles and various embodiments of the invention. Numerous variations and modifications will become apparent to those skilled in the art once the above disclosure is fully appreciated. It is intended that the following claims be interpreted to embrace all such variations and modifications. Although the present disclosure has been described with reference to exemplary embodiments, those skilled in the art will recognize that changes may be made in form and detail without departing from the spirit and scope of the claimed subject matter. For instance, although different exemplary embodiments may have been described as including one or more features providing one or more benefits, it is contemplated that the described features may be interchanged with one another or alternatively be combined with one another in the described example embodiments or in other alternative embodiments, except where indicated to the contrary.

What is claimed is:

1. An orthotic device comprising:
 a flexible support structure comprising
  at least one surface for contacting a body part of a user;
  a plurality of pressure sensors configured for coupling to a microcontroller; and
  a plurality of displacement regions, each said region defining a portion of a flexible support structure, wherein each said portion includes at least one said sensor disposed on or below said at least one surface, and at least one electrically deformable unit,
  wherein each said unit comprises at least one electroactive material and is configured for coupling to said microcontroller wherein:
 a microcontroller coupled to the plurality of pressure sensors and said flexible support structures determines the shape of the flexible support structure based on input from the pressure sensors; and
 wherein the plurality of displacement regions displace the plurality of pressure sensors of the orthotic device when the displacement regions deform.

2. The device of claim 1, wherein at least one said deformable unit comprises a unimorphic structure.

3. The device of claim 1, wherein at least one said deformable unit comprises a multi-morphic structure.

4. The device of claim 1, wherein each said displacement region has, respectively, a first physical configuration when an electrical voltage is not applied to said deformable unit, and has a second physical configuration when an electrical voltage is applied to said deformable unit.

5. The device of claim 4, wherein said second physical configuration increases physical support for a portion of the body part contacting the device compared to said first physical configuration.

6. The device of claim 1 wherein at least one said pressure sensor comprises a piezoelectric material capable of emitting an electrical voltage when depressed.

7. An orthotic module comprising:
 the device of claim 1;
 a power source electrically coupled to said orthotic device and to said microcontroller.

8. The module of claim 7 further comprising:
 an analog to digital converter coupled between said orthotic device and said microcontroller; and
 a digital to analog converter coupled between said microcontroller and said orthotic device.

9. A method of adjusting a dynamically adjustable orthotic device, comprising:

a) coupling the device of claim 1 to a microcontroller and a power source;
b) causing an individual in need of an orthotic device to be positioned so that an external body part of the individual contacts said at least one surface of the device;
c) causing the body part to move and exert pressure on said at least one surface sufficient to depress at least one said sensor, causing each depressed sensor to emit a respective electrical signal indicative of said pressure;
d) operating the microcontroller to measure each said electrical signal, wherein each said measurement is correlated to a physical address of a respective sensor and deformable unit in a said region and includes electrical properties and elapsed time between measurements;
e) operating the microcontroller to determine from said measurements whether any said region requires structural modification to increase or decrease physical support for a portion of said body part in contact with said device; and
f) based on said determination, applying an electrical voltage to at least one deformable unit in a region determined to require said increased physical support, and/or decreasing or ceasing application of an electrical voltage to at least one deformable unit in a region determined to require said decreased physical support, to change the configuration of the orthotic device,
wherein: the microcontroller coupled to the plurality of pressure sensors and said flexible support structures further determines the shape of the flexible support structure based on input from the pressure sensors; and
wherein the plurality of displacement regions displace the plurality of pressure sensors of the orthotic device when the displacement regions deform.

10. The method of claim 9, further comprising:
f) repeating steps b)-e) to adjust the orthotic device during further movement of the body part by the individual, to provide a dynamically adjusted orthodic.

11. The method of claim 9, wherein said body part is a foot of the individual and b)-e) is performed during movement of the foot.

12. The method of claim 9, further comprising, after e) continuously applying said electrical voltage to the orthotic device, to lock the orthotic device into an adjusted configuration.

13. An orthodic manufactured by a process comprising:
obtaining a locked orthodic in accordance with the method of claim 12;
producing a mold from said locked orthotic device; and
applying a resilient polymeric material to said mold to form a permanent orthotic device.

14. A dynamically adjustable orthotic module comprising:
a flexible support structure comprising
at least one surface for contacting a body part of a user;
a plurality of pressure sensors; and
a plurality of displacement regions, each said region defining a portion of said flexible support structure, wherein each said portion includes at least one said sensor disposed on or below said at least one surface, and at least one electrically deformable unit,
wherein each said unit comprises at least one electroactive material;
wherein: a microcontroller coupled to the plurality of pressure sensors determines the shape of the flexible support structure based on input from the pressure sensors and a microcontroller electrically coupled to the plurality of pressure sensors and said flexible support structures, wherein said microcontroller determines the shape of the flexible support structure based on input from the pressure sensors; and
a power source electrically coupled to said flexible support structure and microcontroller,
wherein when the plurality of displacement regions displace the plurality of pressure sensors in the orthotic device when the displacement regions deform.

15. The module of claim 14, further comprising:
an analog to digital converter coupled between said flexible support structure and said microcontroller; and
a digital to analog converter coupled between said microcontroller and said flexible support structure.

16. A method of dynamically adjusting an orthotic module, comprising:
a) causing an individual in need of an orthotic device to be positioned so that an external body part of the individual contacts the at least one surface of the module of claim 14;
b) causing the body part to move and exert pressure on said at least one surface sufficient to depress at least one said sensor, causing each depressed sensor to emit a respective electrical signal indicative of said pressure;
c) operating the microcontroller to measure each said electrical signal, wherein each said measurement is correlated to a physical address of a respective sensor and deformable unit in a said region and includes electrical properties and elapsed time between measurements;
d) operating the microcontroller to determine from said measurements whether any said region requires structural modification to increase or decrease physical support for a portion of said body part in contact with said at least one surface;
e) based on said determination, applying an electrical voltage to at least one deformable unit in a region determined to require said increased physical support, and/or decreasing or ceasing application of an electrical voltage to at least one deformable unit in a region determined to require said decreased physical support, to change the configuration of the orthotic device; and
f) repeating steps b)-e) during further movement of the body part by the individual
wherein: the microcontroller coupled to the plurality of pressure sensors and said flexible support structures further determines the shape of the flexible support structure based on input from the pressure sensors; and
wherein the plurality of displacement regions displace the plurality of pressure sensors of the orthotic device when the displacement regions deform.

17. The method of claim 16 wherein said orthotic module is configured for supporting a foot of the user.

18. The method of claim 17 wherein said power source comprises an air bladder-wind turbine power generator mounted in the shoe of the user.

19. A foot powered energy harvesting device comprising:
a shoe including a chamber, at least a portion of which is surrounded by an electrically conductive coil;
a resilient air bladder disposed in said chamber and containing at least one air inlet valve and at least one air outlet;
at least one air turbine disposed in said chamber, each of which is connected to a respective said air outlet, said air turbine and having blades disposed on a rotatable shaft with magnets thereon, wherein said coil and air turbine are configured to generate electricity when air is expelled from said air bladder outlet causing said shaft to rotate.

20. The device of claim 19, further comprising an energy storage device coupled to said coil.

21. The device of claim 1, wherein a power to flexibly change the shape of the flexible material is derived from a user.

22. The device of claim 14, wherein a power to flexibly change the shape of the flexible material is derived from a user.

* * * * *